United States Patent
Richard et al.

(10) Patent No.: US 6,667,343 B2
(45) Date of Patent: *Dec. 23, 2003

(54) SILOXANE DYES, COMPOSITIONS CONTAINING THEM AND USES THEREOF

(75) Inventors: Hervé Richard, Villepinte (FR); Madeleine Leduc, Paris (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 150 days.

This patent is subject to a terminal disclaimer.

(21) Appl. No.: 09/777,933

(22) Filed: Feb. 7, 2001

(65) Prior Publication Data

US 2002/0155082 A1 Oct. 24, 2002

Related U.S. Application Data

(63) Continuation of application No. 09/142,848, filed as application No. PCT/FR97/00468 on Mar. 14, 1997, now Pat. No. 6,197,911.

(30) Foreign Application Priority Data

Mar. 18, 1996 (FR) .............................. 96 03345

(51) Int. Cl.$^7$ .................. A61K 31/135; A61K 31/695; C07F 7/04; C07F 7/10
(52) U.S. Cl. ......................... 514/647; 514/63; 556/422
(58) Field of Search ......................... 556/422; 514/63, 514/647

(56) References Cited

U.S. PATENT DOCUMENTS

| 2,925,313 A | 2/1960 | Bailey et al. ..................... 8/8 |
|---|---|---|
| 2,963,338 A | 12/1960 | Bailey et al. ..................... 8/8 |
| 3,220,972 A | 11/1965 | Lamoreaux ................. 260/46.5 |
| 3,697,473 A | 10/1972 | Polmanteer et al. .......... 260/37 |
| 4,340,709 A | 7/1982 | Jeram et al. .................. 528/15 |
| 4,381,260 A | 4/1983 | Chu et al. .................... 260/144 |
| 4,892,918 A | 1/1990 | Ryang .......................... 528/15 |
| 5,089,250 A | 2/1992 | Forestier et al. .............. 424/43 |
| 5,685,881 A | 11/1997 | Rose et al. ..................... 8/405 |
| 6,197,911 B1 * | 3/2001 | Richard et al. ............... 528/15 |

FOREIGN PATENT DOCUMENTS

| DE | 3702631 C2 | 8/1987 |
|---|---|---|
| DE | 4240684 A1 | 6/1994 |
| EP | 0287479 A1 | 10/1988 |
| FR | 2642968 A1 | 8/1990 |
| GB | 2018797 A | 10/1979 |

* cited by examiner

Primary Examiner—Russell Travers
(74) Attorney, Agent, or Firm—Finnegan, Henderson, Farabow, Garrett & Dunner, L.L.P.

(57) ABSTRACT

Linear or cyclic diorganosiloxane compounds that include at least one nitroaniline function are disclosed; the compounds may be used as organic dyes in cosmetic compositions suitable for dyeing human keratin fibers, especially hair, or for make-up. The dyes may also be used in foods and pharmaceutical compositions and for dyeing natural and synthetic fibers and plastics or inorganic materials. Also disclosed are the use of the compounds in the above-mentioned fields, cosmetic compositions containing such compounds, and a method for directly dyeing keratin fibers.

16 Claims, No Drawings

SILOXANE DYES, COMPOSITIONS CONTAINING THEM AND USES THEREOF

This application claims benefit under 35 U.S.C. §120 of and is a continuation of application Ser. No. 09/142,848, filed Sep. 17, 1998, now U.S. Pat. No. 6,197,911, which was a national stage application under 35 U.S.C. §371 of PCT/FR97/00468, filed Mar. 14, 1997, all of which are hereby incorporated by reference.

The invention relates to diorganosiloxane compounds containing at least one nitroaniline function, these compounds constituting a novel family of dyes which can be used in the cosmetics field.

Silicon-based dyes have already been described and proposed for coloring natural and synthetic organic fibers or inorganic materials. Such dyes, for instance those described in Belgian Patent Nos. 875,160 and 875,230 or U.S. Pat. Nos. 2,925,313 and 2,963,338, may, however, be reactive because of hydrolysable groups which exist on the silicon atom, thereby possibly giving rise to a certain level of instability or undesirable change under certain conditions of use. This drawback is in addition to the molecular weight, which is sometimes difficult to control.

Polysiloxane dyes containing at least two chromophoric aromatic groups of azo or anthrone type in their chain are known from the prior art. Such dyes are described in U.S. Pat. No. 4,381,260.

In the cosmetics field, and, for example, in hair dyeing, or in the manufacture of make-up products for the lips, the face, the eyelashes and the eyebrows, direct dyes are sought, i.e., dyes which modify the natural shade temporarily, which are of suitable harmlessness and which are stable, in particular with respect to light, to washing and to inclement weather.

The present invention is directed towards obtaining at least one such advantage, by providing novel linear or cyclic diorganosiloxane compounds containing at least one nitroaniline function, which are chemically and physically stable and which have a very good affinity for fibers, in particular for human keratin fibers such as the hair.

These novel compounds may also be of suitable harmlessness, thereby making them particularly suitable for use as dyes in, or for the preparation of, cosmetic compositions intended for dyeing human keratin fibers and in particular the hair, or intended for make-up.

The subject of the present invention is thus compounds which are characterized in that they correspond to one of formulae (1) and (2) below:

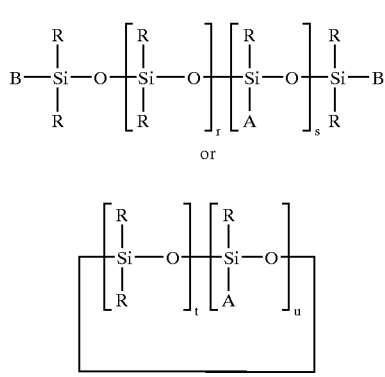

in which formulae (1) and (2):

R, which may be identical or different, are chosen from $C_1$–$C_{10}$ alkyl, phenyl and 3,3,3-trifluoropropyl radicals, at least 80%, on a number basis, of the radicals R being methyl, B, which may be identical or different, are chosen from the above radicals R and the radical A defined below, r is an integer ranging from 0 to 50, and s is an integer ranging from 0 to 20, with the proviso that if s=0 then at least one of the two symbols B denotes A, u is an integer ranging from 1 to 6 and t is an integer ranging from 0 to 10, it being understood that t+u is equal to or greater than 3, and the symbol A denotes a monovalent radical attached directly to a silicon atom, and which corresponds to formula (3) below:

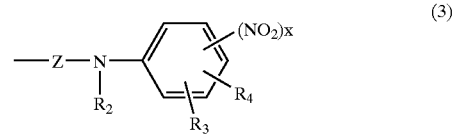

in which formula (3):

Z is chosen from hydrogen and the divalent radical:

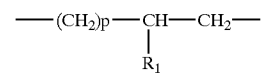

x is 1 or 2, p is an integer ranging from 0 to 10, $R_1$ is chosen from hydrogen and a $C_1$–$C_4$ alkyl radical, $R_2$ is chosen from hydrogen, a $C_1$–$C_4$ alkyl radical and the divalent radical Z defined above, $R_3$ is chosen from hydrogen and a radical $NR_5R_6$ in which $R_5$ and $R_6$, which may be identical or different, are chosen from hydrogen, $C_1$–$C_4$ alkyl radicals, $C_2$–$C_4$ monohydroxyalkyl radicals, $C_2$–$C_4$ dihydroxyalkyl radicals, and the divalent radical Z, it being understood that, in the context of $NR_5R_6$, said at least one radical

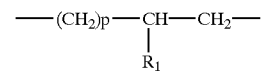

as defined above, $R_4$ is chosen from hydrogen, a hydroxy radical, a halogen radical, a $C_1$–$C_4$ alkyl radical and a $C_1$–$C_4$ alkoxy radical.

In formulae (1) and (2) above, A thus represents the nitroaniline group which, after fixing to the starting silicone chain, imparts dyeing properties to the linear (formula (1)) or cyclic (formula (2)) diorganosiloxane compounds. A is attached to the starting silicone chain via the substituent Z, which therefore must be attached directly to a silicone atom in the chain of either formula (1) or (2), The alkyl radicals defined above for R and B may be linear or branched and chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. In one embodiment of the present invention, the preferred alkyl radicals R and B according to the invention may be chosen from methyl, ethyl, propyl, n-butyl, n-octyl and 2-ethylhexyl radicals. In another embodiment, the radicals R and B are all methyl radicals.

Among the linear or cyclic diorganosiloxanes falling within the scope of the present invention, are random derivatives or derivatives in well-defined blocks having at least one, and in certain embodiments all, of the following characteristics:

R is alkyl such as methyl,

B is alkyl such as methyl (case of the linear compounds of formula (1)), r ranges from 0 to 3; s ranges from 0 to 3 (case of the linear compounds of formula (1)), t+u ranges from 3 to 5 (case of the cyclic compounds of formula (2)), $R_1$ is chosen from hydrogen and methyl, p is equal to 1, x is 1 or 2, $R_2$ and $R_4$ are both hydrogen, R is chosen from hydrogen and a radical $NR_5R_6$ in which $R_5$ and $R_6$, which may be identical or different, are chosen from hydrogen, $C_2$–$C_4$ monohydroxyalkyl radicals, and $C_2$–$C_4$ dihydroxyalkyl radicals, and in one embodiment, all of the following characteristics:

R is alkyl, such as methyl,

B is alkyl, such as methyl (case of the linear compounds of formula (1)),

Z is the divalent radical:

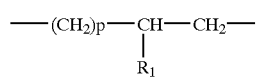

$R_1$ is chosen from hydrogen and methyl, p is equal to 1, r is zero and s is equal to 1 (case of the linear compounds of formula (1)), u=1 and t=2 (case of the cyclic compounds of formula (2)), x is 1 or 2, $R_2$ and $R_4$ are both hydrogen, $R_3$ is is chosen from hydrogen and a radical $NR_5R_6$ in which $R_5$ and $R_6$, which may be identical or different, are chosen from hydrogen, $C_2$–$C_4$ monohydroxyalkyl radicals, and $C_2$–$C_4$ dihydroxyalkyl radicals.

According to the invention, the compounds can be chosen from the following:

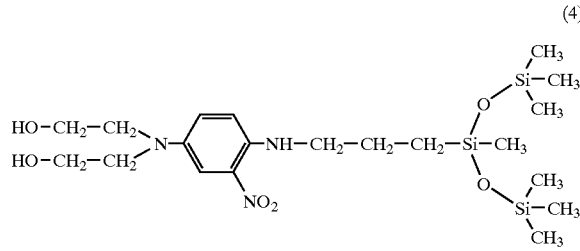

(4)

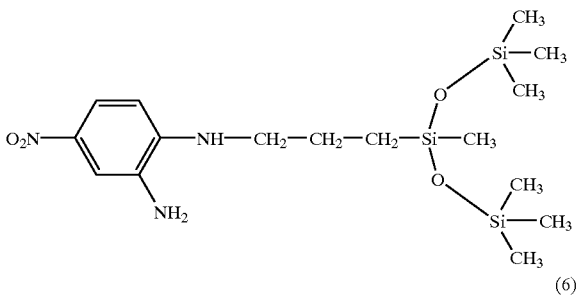

(5)

(6)

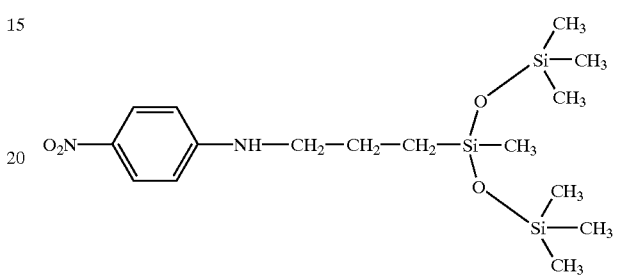

(7)

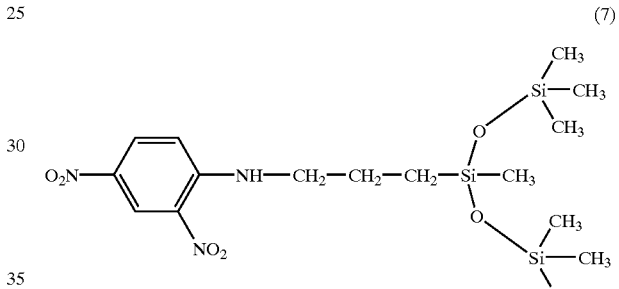

(8)

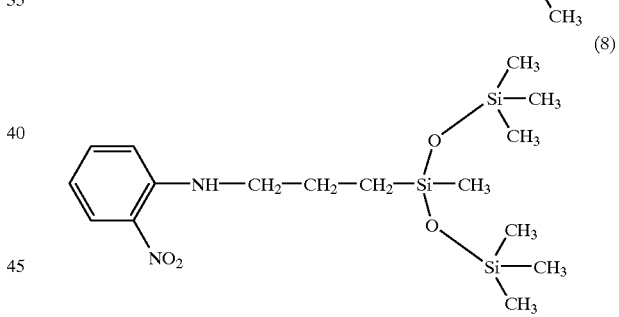

(9)

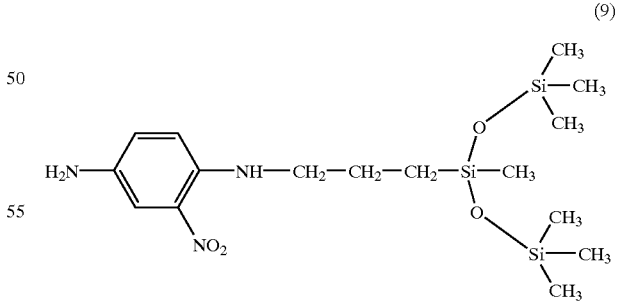

Other exemplary compounds corresponding to formulae (1) and 2 include the following compounds (12)–(14), which represent compounds of formula (1), wherein the substituent A is represented by formula (3). In Formula (12), $R_2$ is equal to Z. Accordingly, the nitrogen atom of formula (3) can be linked to two silicone chains via two divalent radicals Z, as can be seen in Formula (12). In Formula (13), $R_5$ is Z, and in Formula (14), $R_5$ and $R_6$ are both Z, illustrating that the nitrogen atom of $NR_5R_6$ can be linked to one or two silicone chains via one or two radicals Z.

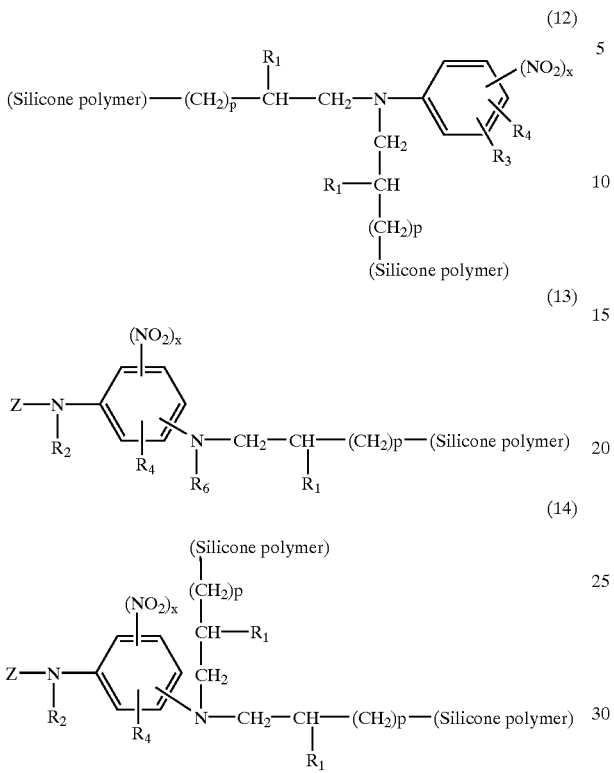

wherein the silicone polymer is a compound selected form formula (1) and formula (2).

In order to prepare the slioxane dyes of formulae (1) and (2), the process may be carried out conventionally (route 1) using a hydrosilylation reaction, namely

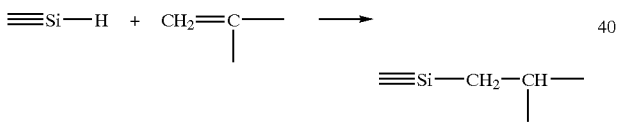

starting with the corresponding silicone, in which, for example, all the radicals A are hydrogen atoms. This starting silicone is referred to hereinbelow as a SiH-containing derivative; the SiH groups may be present in the silicone chain and/or at the ends of the silicone chain. These SiH-containing derivatives are products which are well known in the silicone industry and are generally commercially available. They are described, for example, in U.S. Pat. Nos. 3,220,972, 3,697,473 and 4,340,709, the disclosures of which are hereby incorporated by reference.

This SiH-containing derivative may thus be represented either by formula (1b) below:

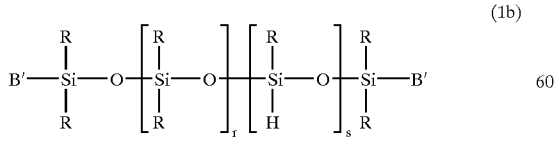

in which R, r and s have the meaning given above for formula (1) and the radicals B', which may be identical or different, are chosen from the radicals R and a hydrogen atom, or by formula (2b) below:

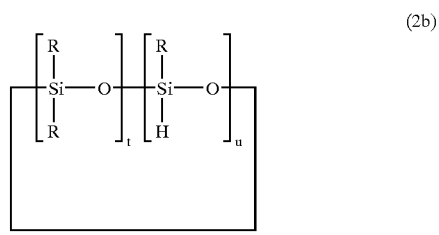

in which R, t and u have the meaning given above for formula (2).

A standard hydrosilylation reaction is thus carried out on this SiH-containing derivative of formula (1b) or (2b), this reaction being performed in the presence of a catalytically effective amount of a platinum catalyst, on a nitroaniline of formula (3b) below:

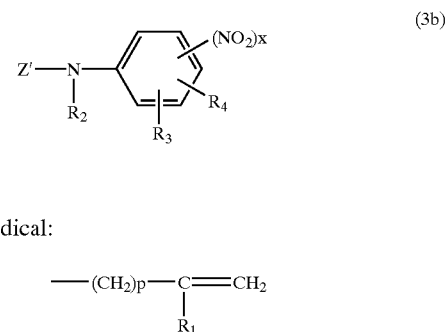

in which,

Z' is the radical:

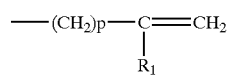

$R_2$ is chosen from hydrogen, $C_1$–$C_4$ alkyl and the radical Z', $R_3$ is chosen from hydrogen and a radical $NR_5R_6$ in which $R_5$ and $R_6$, which may be identical or different, are chosen from hydrogen, $C_1$–$C_4$ alkyl radicals, $C_2$–$C_4$ monohydroxyalkyl radicals, $C_2$–$C_4$ dihydroxyalkyl radicals, and the radical Z', x, p, $R_1$ and $R_4$ have the meaning given above for formula (3), it being understood that, in the context of $NR_5R_6$, said radical Z' is:

—(CH₂)p—C═CH₂
         |
         R₁ as defined above.

Processes which are suitable for the preparation of the products of formula (3b) above are described in particular in German patent application DE-42 40 684.

Another possible synthetic route (route 2) which is suitable for the preparation of the polysiloxane dyes of formulae (1) and (2) comprises starting from the derivatives corresponding to formula (1) or to formula (2) respectively in which all the radicals A are replaced by the radical of formula (10) below:

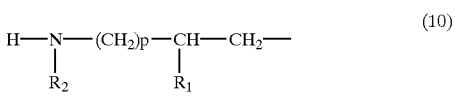

in which $R_1$, $R_2$ and p have the same meaning as in formula (3).

The radicals of formula (10) may be present in the silicone chain and/or at the ends of the silicone chain. These starting aminosiloxane derivatives may thus be represented either by formula (1c) below (linear aminosiloxane derivative):

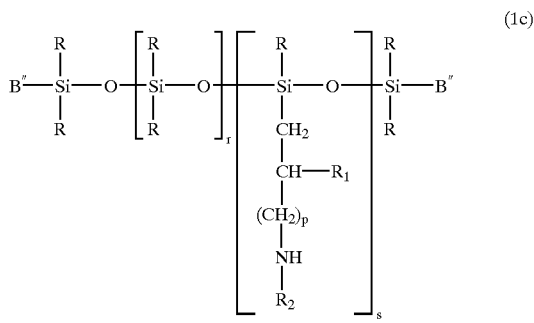

(1c)

in which R, r and s have the meaning given above for formula (1) and the radicals B", which may be identical or different, are chosen from the radicals R and the radical of formula (10), or by formula (2c) below (cyclic aminosiloxane derivative):

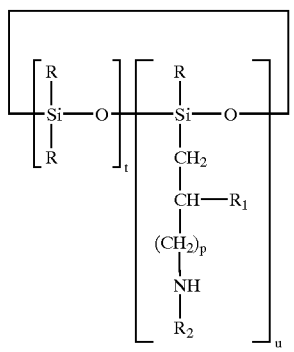

(2c)

in which R, t and u have the meaning given above for formula (2).

The aminosiloxane derivatives of formula (1c) or (2c) above are products which are well known in the silicone industry and are generally commercially available. They are moreover described in particular in German patent application DE-A 37 02631.

These aminosiloxane derivatives are then reacted with the halo derivative of formula (11) below:

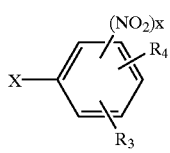

(11)

X more particularly being fluorine or chlorine, and even more particularly fluorine.

The subject of the present invention is also the use of the compounds of formula (1) or (2) as dyes in a cosmetic, pharmaceutical or food composition or in a dye composition intended for dyeing natural or synthetic fibers, or inorganic or plastic materials.

The subject of the invention is thus also a cosmetic composition comprising, in a cosmetically acceptable medium, an effective amount of at least one compound of formula (1) or (2) defined above.

The compounds of formula (1) or (2) may be present in proportions ranging from 0.01 to 10%, such as from 0.1 to 5%, by weight relative to the total weight of the cosmetic composition.

When the composition of the invention is a cosmetic composition, it may be used as a dye composition for keratin fibers and in particular as a direct dye composition for the hair, as a composition for the oxidation dyeing of the hair, containing at least one oxidation dye and the compound or compounds of formula (1) or (2) as direct dyes. It may also be used as a make-up composition such as products for the lips or the face, the eyelashes, the eyebrows, a lipstick, an eyeshadow, a blusher, a foundation, an eyeliner, a mascara or a nail varnish.

The cosmetically acceptable medium can be, in this case, a medium comprising water and/or cosmetically acceptable organic solvents, and more particularly alcohols, glycols or glycol ethers, in concentrations ranging from 0.5 to 20%, such as from 2 to 10%, by weight relative to the total weight of the composition. It may also contain fatty substances such as oils and waxes.

The said cosmetic composition may also contain any other adjuvant commonly used in cosmetics, according to the application envisaged, and, for example, surfactants which are well known in the state of the art and of anionic, cationic, nonionic, amphoteric or zwitterionic type or mixtures thereof, thickeners, antioxidants, fragrances, sequestering agents, dispersing agents, packaging agents, preserving agents, opacifiers, etc.

A person skilled in the art will take care to select the optional additional compound or compounds mentioned above, such that at least one of the advantageous properties intrinsically associated with the dye composition according to the invention is not, or is substantially not, adversely affected by the addition or additions envisaged.

The cosmetic composition according to the invention may be formulated at acidic, neutral or alkaline pH, it being possible for the pH to vary, for example, from 4 to 11, such as from 5 to 10, and for it to be adjusted using previously well-known basifying or acidifying agents.

The invention also relates to a process for dyeing human keratin fibers, and in particular the hair, by direct dyeing, by leaving a dye composition containing at least one dye of formula (1) or (2) on wet or dry keratin fibers. The composition according to the invention may be used as a leave-in composition, that is, after applying the composition to the fibers, they are dried without intermediate rinsing. In the other modes of application, the composition is left to act on the fibers for an exposure time ranging from 3 to 60 minutes, such as from 5 to 45 minutes, after which the fibers are rinsed, optionally washed, rinsed again and dried.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The examples which follow illustrate the invention without, however, limiting the scope thereof.

EXAMPLE 1

5.62 g (0.02 mol) of the compound of formula

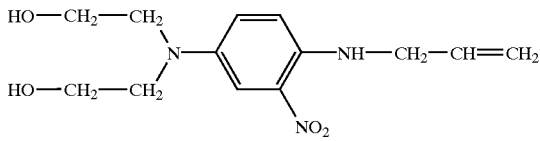

20 ml of anhydrous toluene and 100 µl of platinum catalyst (complex containing 3–3.5% Pt in cyclovinylmethylsiloxane, sold by the company Hüls under the brand name Petrarch PC085) were introduced into a fully equipped round-bottomed flask. The mixture was brought to 80° C. under nitrogen and 5.56 g (0.025 mol) of heptamethyltrisiloxane were then added dropwise. After stirring for three hours at 80° C. under nitrogen, the medium was concentrated and the solvent and the excess siloxane were evaporated off.

The oil obtained was chromatographed on silica (eluent: 50/50 heptane/ethyl acetate). 10.1 g of the siloxane dye of formula (4):

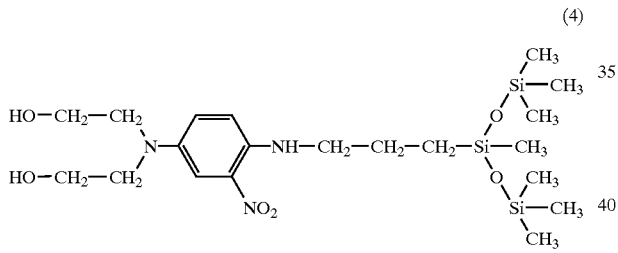

(4)

were thus recovered in the form of a thick deep-velvet oil:

| Elemental analysis for $C_{20}H_{41}N_3O_6Si_3$ | | | | |
| --- | --- | --- | --- | --- |
| theory: | C 47.68 | H 8.20 | N 8.34 | Si 16.72 |
| found: | C 47.75 | H 8.18 | N 8.19 | Si 16.54 |

EXAMPLE 2

9.66 g (0.05 mol) of the compound of formula.

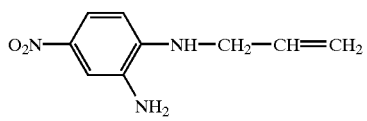

50 ml of anhydrous toluene and 100 µl of platinum catalyst (complex containing 3–3.5% Pt in cyclovinylmethylsiloxane, sold by the company Hüls under the brand name Petrarch PC085) were introduced into a fully equipped round-bottomed flask. The mixture was brought to 75° C. under nitrogen and 13.35 g (0.06 mol) of heptamethyltrisiloxane were then added dropwise. After stirring for six hours at 80° C. under nitrogen, the medium was concentrated and the solvent and the excess siloxane were evaporated off.

The oil obtained was chromatographed on silica (eluent: 50/50 heptane/$CH_2C_{12}$). 9.9 g of the siloxane dye of formula (5):

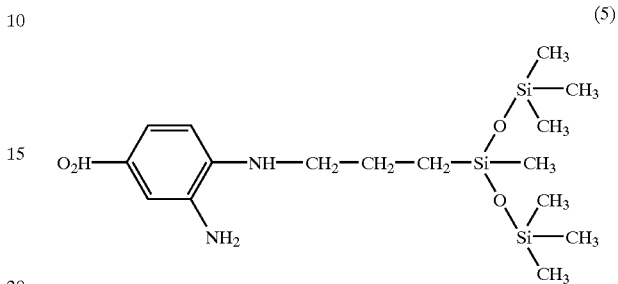

(5)

were thus recovered in the form of a red powder:

| Melting point: 52–53° C. | | | |
| --- | --- | --- | --- |
| Elemental analysis for $C_{16}H_{33}N_3O_4Si_3$ | | | |
| theory: | C 46.23 | H 8.00 | N 10.11 | Si 20.27 |
| found: | C 46.40 | H 7.95 | N 10.16 | Si 20.16 |

EXAMPLE 3

17.8 g (0.1 mol) of the compound of formula:

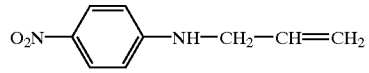

100 ml of anhydrous toluene and 100 µl of platinum catalyst (complex containing 3–3.5% Pt in cyclovinylmethylsiloxane, sold by the company Hüls under the brand name Petrarch PC085) were introduced into a fully equipped round-bottomed flask. The mixture was brought to 80° C. under nitrogen and 24.5 g (0.11 mol) of heptamethyltrisiloxane were then added dropwise. After stirring for four hours at 80° C. under nitrogen, the medium was concentrated and the solvent and the excess siloxane were evaporated off.

The oil obtained was crystallized from a water/ethanol mixture. 18.7 g of the siloxane dye of formula (6):

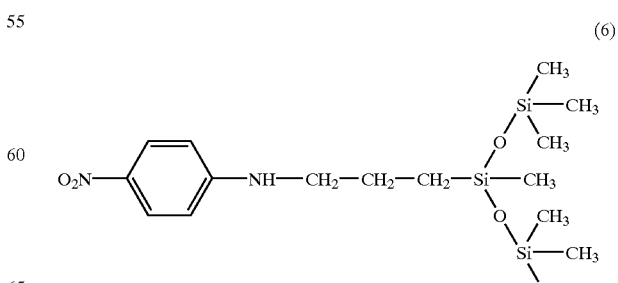

(6)

were thus recovered in the form of a yellow powder:

| | Melting point: 39–40° C. | | |
|---|---|---|---|
| | Elemental analysis for $C_{16}H_{32}N_2O_4Si_3$ | | |
| theory: | C 47.96 | H 8.05 | N 6.99 | Si 21.03 |
| found: | C 47.85 | H 8.31 | N 6.71 | Si 20.94 |

EXAMPLE 4

4.46 g (0.02 mol) of the compound of formula:

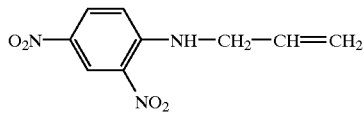

20 ml of anhydrous toluene and 20 μl of platinum catalyst (complex containing 3–3.5% Pt in cyclovinylmethylsiloxane, sold by the company Hüls under the brand name Petrarch PC085) were introduced into a fully equipped round-bottomed flask. The mixture was brought to 70° C. under nitrogen and 4.5 g (0.04 mol) of heptamethyltrisiloxane were then added dropwise. After stirring for three hours at 80° C. under nitrogen, the medium was concentrated and the solvent and the excess siloxane were evaporated off.

The oil obtained was chromatographed on silica (eluent: 90/10 heptane/$CH_2$–$C_{12}$). 5.2 g of the siloxane dye of formula (7):

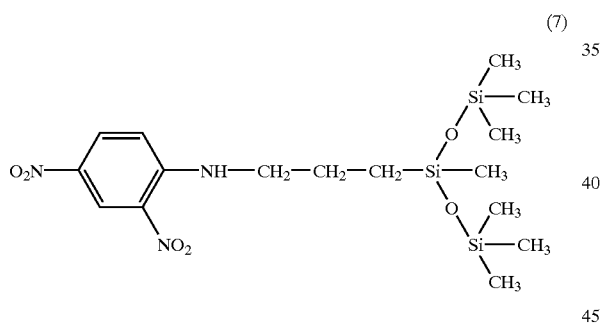

were thus recovered in the form of an orange-yellow powder:

| | Melting point: 56–57° C. | | |
|---|---|---|---|
| | Elemental analysis for $C_{16}H_{31}N_3O_6Si_3$ | | |
| theory: | C 43.12 | H 7.01 | N 9.43 | Si 18.90 |
| found: | C 43.14 | H 7.08 | N 9.41 | Si 19.05 |

EXAMPLE 5

8.5 g (0.05 mol) of the compound of formula:

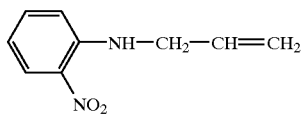

50 ml of anhydrous toluene and 100 μl of platinum catalyst (complex containing 3–3.5% Pt in cyclovinylmethylsiloxane, sold by the company Hüls under the brand name Petrarch PC085) were introduced into a fully equipped round-bottomed flask. The mixture was brought to 70° C. under nitrogen and 13.35 g (0.06 mol) of heptamethyltrisiloxane were then added dropwise. After stirring for three hours at 80° C. under nitrogen, the medium was concentrated and the solvent and the excess siloxane were evaporated off.

The oil obtained was chromatographed on silica (eluent: heptane). 14.8 g of the siloxane dye of formula (8):

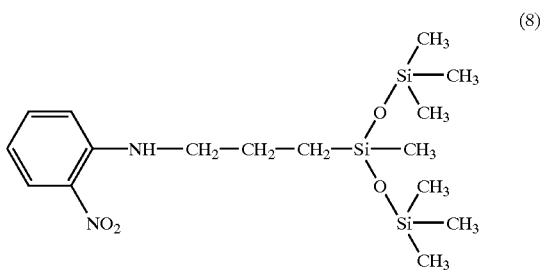

were thus recovered in the form of an orange-colored oil:

| | Elemental analysis for $C_{16}H_{32}N_2O_4Si_3$ | | |
|---|---|---|---|
| theory: | C 47.96 | H 8.05 | N 6.99 | Si 21.03 |
| found: | C 48.04 | H 7.96 | N 6.92 | Si 20.76 |

EXAMPLE 6

1.675 g (0.0107 mol) of the compound of formula:

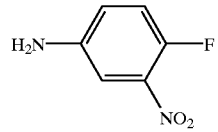

5 ml of anhydrous dioxane and 3 g (0.0107 mol) of the compound of formula.

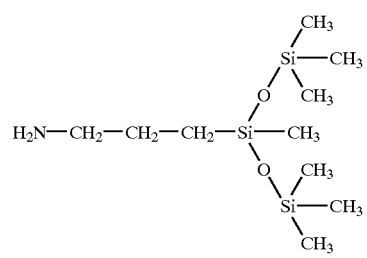

were introduced into a fully equipped round-bottomed flask. The mixture was brought to 70° C. under nitrogen for seven hours. The mixture was filtered when cold and the filtrate was concentrated. The residue was crystallized from an 80/20 water/ethanol mixture. 0.2 g of the siloxane dye of formula (9):

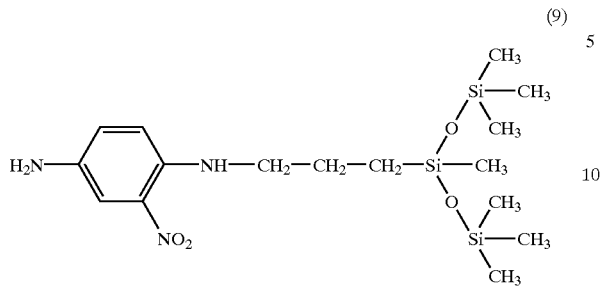

was thus recovered in the form of a black-red powder:

| Melting point: 81–82° C. Elemental analysis for $C_{16}H_{33}N_3O_4Si_3$ | | | | |
|---|---|---|---|---|
| theory: | C 46.23 | H 8.00 | N 10.11 | Si 20.27 |
| found: | C 46.26 | H 8.04 | N 9.92 | Si 20.50 |

EXAMPLE 7

Locks of natural grey hair containing 90% white hairs were dyed with a dye composition containing $5\times10^{-2}$ mol of the dye prepared in Example 6, in an amount of a mixture of ethanol and water (90/10 by weight) which was sufficient to bring the composition to 100 g.

After treatment for 30 minutes, the hair was rinsed with water for 5 minutes and then dried.

The locks of hair were dyed a violet-red color.

EXAMPLE 8

Locks of natural grey hair containing 90% white hairs were dyed with a dye composition containing $5\times10^{-2}$ mol of the dye prepared in Example 2, in an amount of a mixture of ethanol and water (90/10 by weight) which was sufficient to bring the composition to 100 g.

After treatment for 30 minutes, the hair was rinsed with water for 5 minutes and then dried.

The locks of hair were dyed an orange-yellow color.

What is claimed is:
1. A compound chosen from compounds of formula (1):

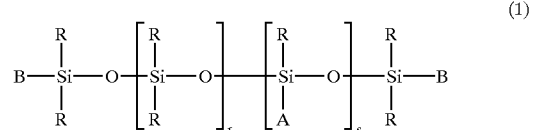

and formula (2)

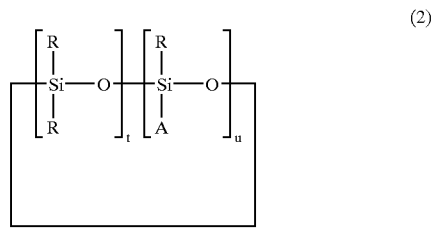

in which:
R are independently chosen from linear and branched $C_1$–$C_{10}$ alkyl, phenyl and 3,3,3-trifluoropropyl radicals, wherein at least 80%, on a number basis, of radicals R are methyl,
A is chosen from monovalent radicals linked directly to a silicon atom corresponding to formula (3):

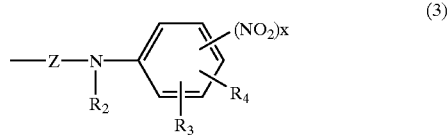

wherein:
Z is the divalent radical:

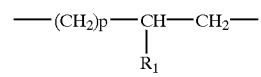

x is 1 or 2,
p is an integer ranging from 0 to 10,
$R_1$ is chosen from hydrogen and $C_1$–$C_4$ alkyl radicals,
$R_2$ is chosen from hydrogen, $C_1$–$C_4$ alkyl radicals, and said divalent radical Z,
$R_3$ is chosen from hydrogen and radicals NR $R_5R_6$, wherein $R_5$ and $R_6$ independently are chosen from hydrogen, $C_1$–$C_4$ alkyl radicals, $C_2$–$C_4$ mono- and dihydroxyalkyl radicals, and said divalent radical Z, with the proviso that at least one of $R_2$, $R_5$ and $R_6$ is said divalent radical Z,
$R_4$ is chosen from hydrogen, a hydroxy radical, a halogen radical, $C_1$–$C_4$ alkyl radicals and $C_1$–$C_4$ alkoxy radicals;
B are independently chosen from said radicals R and radical A,
r is an integer ranging from 0 to 50,
s is an integer ranging from 0 to 20, with the proviso that if s is zero then at least one of the two symbols B denotes A,
u is an integer ranging from 1 to 6, and
t is an integer ranging from 0 to 10, with the proviso that the sum of t+u is at least 3.
2. A compound according to claim 1, wherein said radicals R are chosen from linear and branched $C_1$–$C_{10}$ alkyl radicals.
3. A compound according to claim 2, wherein said radicals R are chosen from methyl, ethyl, propyl, n-butyl, n-octyl and 2-ethylhexyl radicals.
4. A compound according to claim 3, wherein said radicals R are methyl radicals.
5. A compound according to claim 1, wherein in formula (1), said radicals B are chosen from linear and branched $C_1$–$C_{10}$ alkyl radicals.

6. A compound according to claim 5, wherein said radicals B are chosen from methyl, ethyl, propyl, n-butyl, n-octyl and 2-ethylhexyl radicals.

7. A compound according to claim 6, wherein said radicals B are methyl radicals.

8. A compound according to claim 1, wherein said compound corresponds to formula (1), wherein r ranges from 0 to 3 and s ranges from 0 to 3.

9. A compound according to claim 8, wherein r is 0 and s is 1.

10. A compound according to claim 1, wherein said compound corresponds to formula (2) wherein the sum of t+u ranges from 3 to 5.

11. A compound according to claim 10, wherein t is 2 and u is 1.

12. A compound according to claim 1, wherein $R_1$ is chosen from hydrogen and methyl.

13. A compound according to claim 7, wherein said radicals R are methyl radicals.

14. A compound according to claim 1, wherein p is 1.

15. A compound according to claim 1, wherein $R_2$ and $R_4$ are hydrogen.

16. A compound according to claim 1, wherein $R_3$ is chosen from hydrogen and radicals $NR_5R_6$ wherein $R_5$ and $R_6$ independently are chosen from hydrogen and $C_2$–$C_4$ mono- and dihydroxyalkyl radicals, with the proviso that $R_2$ is said divalent radical Z.

* * * * *

UNITED STATES PATENT AND TRADEMARK OFFICE
CERTIFICATE OF CORRECTION

PATENT NO.     : 6,667,343 B2
DATED          : December 23, 2003
INVENTOR(S)    : Hervé Richard et al.

It is certified that error appears in the above-identified patent and that said Letters Patent is hereby corrected as shown below:

<u>Column 14,</u>
Line 40, "NR $R_5R_6$," should read -- $NR_5R_6$, --.

Signed and Sealed this

Sixth Day of April, 2004

JON W. DUDAS
*Acting Director of the United States Patent and Trademark Office*